United States Patent [19]

Hachmann

[11] Patent Number: Plant 6,026

[45] Date of Patent: Sep. 29, 1987

[54] RHODODENDRON PLANT—SAMMETGLUT VARIETY

[75] Inventor: Hans Hachmann, Barmstedt in Holstein, Fed. Rep. of Germany

[73] Assignee: The Conard-Pyle Company, West Grove, Pa.

[21] Appl. No.: 631,718

[22] Filed: Jul. 17, 1984

[51] Int. Cl.[4] ..... A01H 5/00

[52] U.S. Cl. ..... Plt./57

[58] Field of Search ..... Plt./57

*Primary Examiner*—Robert E. Bagwill

*Attorney, Agent, or Firm*—Burns, Doane, Swecker & Mathis

[57] ABSTRACT

A new and distinct variety of Rhododendron plant which originated as a chance seedling in a cultivated area is provided. The new variety produces flowers which are of a highly attractive clear bright red coloration on a well-branched compact plant which exhibits good tolerance to extremes in temperature.

1 Drawing Figure

SUMMARY OF THE INVENTION

The new variety of Rhododendron plant was discovered and selected by me as a chance seedling found in the cultivated state in my hybridizing house at my nursery at Barmstedt in Holstein, West Germany among many other plants. The parents of the new variety are unknown.

A portion of my Rhododendron breeding in the hybridizing house had been devoted to the creation of hardy, large flowered types which will offer improvement over existing varieties of these very popular plants. The present selection resulted from my desire to provide a hardy red Rhododendron plant which had a cleaner and brighter blossom coloration than the best known hardy varieties in this color range, Nova Zembla and America (non-patented), both of which have a decided magenta-blue cast to their blossoms. This object was successfully achieved, and the new variety exhibits a combination of characteristics which distinguish it from all other hardy red flowered Rhododendron cultivars of which I am aware.

The following combination of characteristics is exhibited by the new variety of Rhododendron plant:

(a) a well-branched, compact plant of good vigor, (b) very attractive blossoms having a clear, bright red coloration which contrasts handsomely with the white stamens, (c) winter hardiness to −25° C., and (d) an aptitude for rooting from mature cuttings which compares favorably with presently known varieties.

The winter hardiness to −25° C. was determined with respect to 2- to 3-year old plants growing in the landscape at Barmstedt in Holstein, West Germany.

Asexual reproduction of my new variety by cuttings has been accomplished by grafting at Barmstedt in Holstein, West Germany, and at West Grove, Pa., and by grafting at Barmstedt in Holstein, West Germany, thereby demonstrating that the unique combination of characteristics has been established and is transmitted to successive generations.

The new variety has been named the Sammetglut variety. Plants of the new variety are being marketed by The Conard-Pyle Company under the Crimson Classic trademark.

BRIEF DESCRIPTION OF THE PHOTOGRAPH

The accompanying photograph illustrates typical specimens of the blossoms, foliage, and stems of the new variety as depicted in color as true as is reasonably possible to make the same in a color illustration of this character. The specimens illustrated were three years old and were being grown in a soilless medium during the second half of May at West Grove, Pa.

DETAILED DESCRIPTION

The following is a detailed description of the new Rhododendron variety with color terminology in accordance with the R.H.S. Colour Chart of The Royal Horticultural Society, London, England. The description was prepared using specimens of representative three year-old plants growing in a soilless medium during late May at West Grove, Pa.

Field grown 8- to 10-year old plants of the new variety located at U.S.D.A. Zone Nos. 6 and 7 are anticipated to assume a height of approximately 48 to 54 inches and a width of approximately 42 to 48 inches.

Field grown 5-year old plants of the new variety at the same location commonly exhibit a height of approximately 36 inches and a width of approximately 30 inches.

Foliage:

*Type.*—Evergreen, leaves lancolate, apex acute, base obtuse, and margins entire.

*Size.*—Length of mature leaves growing midway up the stem — approximately 9 to 13 cm. with an average of approximately 11.5 cm., and a width of mature leaves growing midway up the stem — approximately 4.3 to 5.8 cm. with an average of approximately 5.0 cm.

*Color.*—Mature leaves, upper surface Green Group 137A, and under surface Green Group 138B.

Branches:

*Color.*—Mature wood, one year old — Green Group 143C, tinged with Red Group 45D. Mature wood, current year — Red Group 53B, with green highlights.

Flower:

*Size.*—Individual floret size approximately 3.5 to 4.5 cm. in diameter. Flower truss size approximately 9.5 to 11.5 cm. in diameter.

*Color.*—Fully open flowers — near Red Group 45B and 45C.

I claim:

1. A new and distinct variety of Rhododendron plant, substantially as herein shown and described, characterized particularly as to novelty by the unique combination of:

(a) a well-branched, compact plant of good vigor,
(b) very attractive blossoms having a clean, bright red color, which contrasts handsomely with the white stamens,
(c) winter hardiness to −25° C., and
(d) an aptitude for rooting from mature cuttings which compares favorably with presently known varieties.

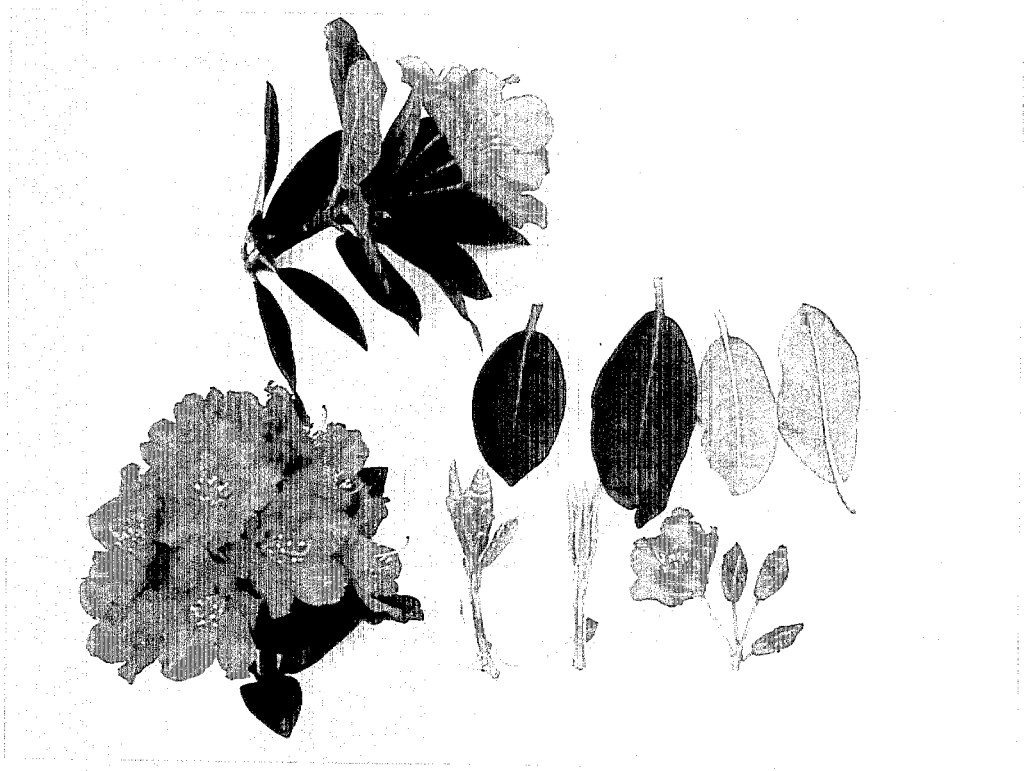

* * * * *